United States Patent
Smith et al.

(10) Patent No.: US 7,678,067 B1
(45) Date of Patent: Mar. 16, 2010

(54) APPARATUS FOR PROVIDING DORSIFLEXION ASSISTANCE IN ANKLE FOOT ORTHOSES AND NIGHT SPLINTS

(76) Inventors: Cleveland C. Smith, 412 Albert, Helena, MT (US) 59601; Jared O'Connor, 1627 Peosia Ave., Helena, MT (US) 59601

(*) Notice: Subject to any disclaimer, the term of this patent is extended or adjusted under 35 U.S.C. 154(b) by 212 days.

(21) Appl. No.: 11/784,858

(22) Filed: Apr. 9, 2007

Related U.S. Application Data

(60) Provisional application No. 60/790,200, filed on Apr. 7, 2006.

(51) Int. Cl.
*A61F 5/00* (2006.01)
(52) U.S. Cl. .......................... 602/23; 602/27
(58) Field of Classification Search ............ 602/5, 602/16, 23, 26, 27; 128/882; 482/79, 120, 482/121, 123
See application file for complete search history.

(56) References Cited

U.S. PATENT DOCUMENTS

| | | | |
|---|---|---|---|
| 5,215,508 A | 6/1993 | Bastow | |
| 5,224,925 A | 7/1993 | Varn | |
| 5,291,904 A * | 3/1994 | Walker | 128/882 |
| 5,486,157 A | 1/1996 | Di Benedetto | |
| D385,358 S | 10/1997 | Carlson | |
| 5,700,237 A | 12/1997 | Hess | |
| 5,860,423 A | 1/1999 | Thompson | |
| 6,056,712 A | 5/2000 | Grim | |
| 6,063,013 A * | 5/2000 | Vathappallil | 482/121 |
| 6,267,742 B1 | 7/2001 | Krivosha et al. | |
| 6,302,858 B1 | 10/2001 | De Toro et al. | |
| 6,514,254 B1 | 2/2003 | Falls | |
| 6,793,638 B1 | 9/2004 | De Toro et al. | |
| 6,824,523 B2 | 11/2004 | Carlson | |
| 6,926,687 B2 * | 8/2005 | Shields | 602/24 |
| 7,112,181 B1 | 9/2006 | De Toro et al. | |
| 7,410,472 B2 * | 8/2008 | Yakimovich et al. | 602/16 |

* cited by examiner

*Primary Examiner*—Michael A. Brown
(74) *Attorney, Agent, or Firm*—Todd N. Hathaway

(57) ABSTRACT

An apparatus for providing dorsiflexion assistance in an orthotic device having ankle and foot sections joined by a hinge connection. The orthotic device may be, for example, an ankle foot orthotic or a night splint. The apparatus includes an elastic member, such as an elastomeric strap, having a first end that is attached to an upper portion of the ankle section of the orthotic device, and a cable that connects a second end of the elastic member to the foot section of the device at a position that is spaced anteriorly from the hinge connection, so that tension supplied by the elastic member creates dorsiflexion torque about the hinge connection. A tension adjuster is provided to allow the amount of torque to be adjusted to meet individual needs. An optional cable guard protects the cable from interference, and can also be used as a cable stop that effectively increases dorsiflexion force to compensate for loss of tension due to shortening of the elastic member upon dorsiflexion. The cable member may be attached to the foot section by routing it through a channel in a bridge piece under the arch area of the foot section of the device. The characteristics and amount of torque can be adjusted by adjusting the distance by which the cable attachment is spaced anteriorly (forward) of the hinge connection. The assist apparatus can readily be mounted to existing orthotic devices without requiring significant modification of the latter.

9 Claims, 8 Drawing Sheets

PRESENT INVENTION

APPARATUS FOR PROVIDING DORSIFLEXION ASSISTANCE IN ANKLE FOOT ORTHOSES AND NIGHT SPLINTS

RELATED CASES

This application claims the benefit of U.S. Provisional Patent Application Ser. No. 60/790,200 filed on Apr. 7, 2006.

BACKGROUND

1. Field of Invention

The present invention relates generally to ankle foot orthoses (AFOs), and, more particularly, to AFOs which assist in dorsiflexion of the foot.

2. Related Art

Foot drop in a patient can result from several causes. The most common are physical trauma to the tibial nerve, multiple sclerosis, spinal injury and strokes. As a result a person may loose the tone and the ability to contract the dorsal flexors of the foot. This in turn causes a problem termed "foot drop" in which the person points their foot when walking, which results in the person increasing their height of gait in an effort to avoid tripping or dragging their own foot.

The industry has responded to this condition with devices that actively resist plantar flexion. Several early devices utilized a torsion spring in the hinge joint of the AFO. This was only marginally successful, since the joint was large and the spring lost torsion quickly as the foot dorsiflexed.

A more modern device is the Tamarack™ joint developed by Carlson (U.S. Pat. No. D385,358). This device is still widely used today, and is relatively inexpensive to produce, easy to install, and performs successfully in a moderate amount of cases. Nevertheless, it possesses several drawbacks.

For example, in order to use the Tamarack™ joint an AFO must be vacuum-formed specifically for that joint. If it turns out that the patient does not like dorsiflexion assist the AFO can not be changed over to a conventional AFO, and therefore a new AFO must be built. Conversely, patients that have a deteriorating condition, such as MS, may have no need for dorsiflexion assist initially, but in time may deteriorate to a point that need arises in this case; the previously built conventional AFO will need to be discarded and replaced with a new brace incorporating the Tamarack™ joint. This is time consuming and costly. Furthermore, the manner in which the mechanism applies torque is not optimal for treating foot drop: Because the joint relies only on the elongation of the elastic material, as the material stretches the amount of torque exerted through the joint increases more-or-less linearly, i.e., the farther the joint is plantarflexed the more torque it exerts. This is counter to the biomechanics of the foot, since, at a standing position, the calf muscles are not tensed and do not offer much resistance, but as the foot is dorsal-flexed the calf muscles resist due to tension being applied to them through a stretch reflex. However, the Tamarack™ joint rapidly loses tension as the foot is dorsiflexed, and as a result loses the ability to properly dorsiflex the foot. Furthermore, the joint is limited to a peak torque of approximately 2.5 foot/pounds; in many cases this is inadequate to properly dorsiflex the foot, especially with large persons or persons exhibiting spasticity.

The device shown in U.S. Pat. No. 6,752,774 tries to rectify several weaknesses in the Tamarack™ joint. This device addresses the loss in torque by using moment arms to create the torque. This in turn produces torque more uniformly through the range of motion. The device utilizes two hooks over which a small strip of rubber tubing is stretched; as the AFO is plantar-flexed the tubing is stretched and its elasticity creates tension. There are several disadvantages to this ankle joint: It is very large and cumbersome, creating fabrication problem for the orthopedist, and as with the Tamarack™ it requires that the AFO be specifically made for the joint.

The device shown in U.S. Pat. No. 6,602,217 approached this problem using an elastic strap attached at a location proximate the first metatarsal of the foot. This has several problems in that dorsiflexing the foot results in the elastic material rapidly decreasing in length, leading to a rapid fall-off in tension. This decrease in tension is undesirable. Moreover, the path of the elastic material is undesirable as the shoe may interfere with it and render the device unusable.

In summary, existing devices fail to address the biomechanical properties of the ankle joint with proper torque curves. This results in incomplete dorsiflexion and fails to meet the requirements of many individuals, especially those who fall outside the norm. The dorsiflexion assist devices in use today also cannot be incorporated into or adapted to existing AFOs, and therefore require that AFOs be fabricated specifically for their use.

The issues noted above have been discussed in the context of AFOs, but it will be understood that they pertain to dorsiflexion assist devices that are used with night splints as well.

Accordingly, there exists a need for a dorsiflexion assist device for use with ankle foot orthoses and night splints that applies torque in a manner consistent with the biomechanics of the patient's foot. Furthermore, there exists a need for such an apparatus that is adapted to and used with existing AFOs and night splints, so that fabrication of a special AFO or night splint is not required in order to be able to provide dorsiflexion assistance. Still further, there exists a need for such an apparatus that allows the torque characteristics to be adjusted to meet the specific needs of the patient. Still further, there exists a need for such an apparatus that is not bulky and that can be used without interference being caused by a shoe. Still further, there exists a need for such an apparatus that is durable and long-lasting, and that will not lose effectiveness over an extended period of use.

SUMMARY OF THE INVENTION

The present invention has solved the problems cited above. Broadly, there is an apparatus for providing dorsiflexion assistance for an orthotic device having an ankle section and a foot section joined by a hinge connection, the apparatus comprising: (a) at least one elastic member, (b) means for attaching a first end of the elastic member to the ankle portion of the orthotic device, (c) at least one cable member mounted to a second end of the elastic member, and (d) means for attaching the cable member to the foot section of the orthotic device at a location spaced anteriorly from the hinge connection, (e) so that tension created on the cable member by the elastic member creates dorsiflexion torque about the hinge connection of the orthotic device.

The apparatus may further comprise means for adjusting the tension on the at least one elastic member. The elastic member may comprise an elastic strap member, and the means for adjusting tension on the elastic member may comprise an adjustable buckle member for selectively tightening the elastic strap member. The at least one elastic member may comprise first and second elastic members for being mounted on opposite sides of the ankle section of the orthotic device.

The means for attaching the first end of the elastic member to the ankle section of the orthotic device may comprise means for attaching the first end of the elastic member to an upper portion of the ankle section of the device at a location that is spaced anteriorly from the hinge connection.

The means for attaching the cable member to the foot section of the orthotic device may comprise a bridge formed across a bottom surface of the foot section of the orthotic device, under which the cable member is passed so that tension on the cable member is equalized on opposite sides of the orthotic device. The bridge may comprise a transversely extending channel that receives the cable member therein.

The apparatus may further comprise a guard member that is mountable to the foot section of the orthotic device so as to prevent interference with the cable member. The guard member may comprise a generally vertically extending channel portion that captures the cable member so as to arrest rearward movement of the cable member at a predetermined location, so as to create a moment arm that compensates for reduced tension resulting from shortening of the elastic member during dorsiflexion of the foot section. The guard member may further comprise means for mounting the guard member so that the cable member is arrested at a location approximately in vertical alignment with a pivot axis of the hinge connection.

The orthotic device may be an ankle foot orthotic, or may a night splint.

The invention also provides an orthotic assembly that provides dorsiflexion assistance, the orthotic assembly comprising: (a) an ankle section, (b) a foot section, (c) a hinge connection interconnecting the ankle section and the foot section, (d) at least one elastic member having a first end that is attached to the ankle section, and (e) at least one cable member having a first end that is attached to a second end of the elastic member, and a second end that is attached to the foot section of the orthotic assembly at a location spaced anteriorly from the hinge connection, (f) so that tension exerted on the cable member by the elastic member creates dorsiflexion torque about the hinge connection of the orthotic assembly.

The invention further provides a method for providing dorsiflexion assistance in an orthotic device having an ankle section and a foot section interconnected by a hinge connection, the method comprising the steps of: (a) providing a dorsiflexion assistance apparatus comprising an elastic member having a first end and a second end, and a cable member having first and second ends, the first end of the cable member being attached to the second end of the elastic member, (b) attaching the first end of the elastic member to the ankle section of the orthotic device, and (c) attaching the second end of the cable member to the foot section of the orthotic device at a position spaced anteriorly from the pivot connection, (d) so that tension created on the cable member by the elastic member creates dorsiflexion torque about the hinge connection of the orthotic device.

These and other features and advantages of the present invention will be more fully appreciated from a reading of the following detailed description with reference to the accompanying drawings.

DETAILED DESCRIPTION

Figure 1A:
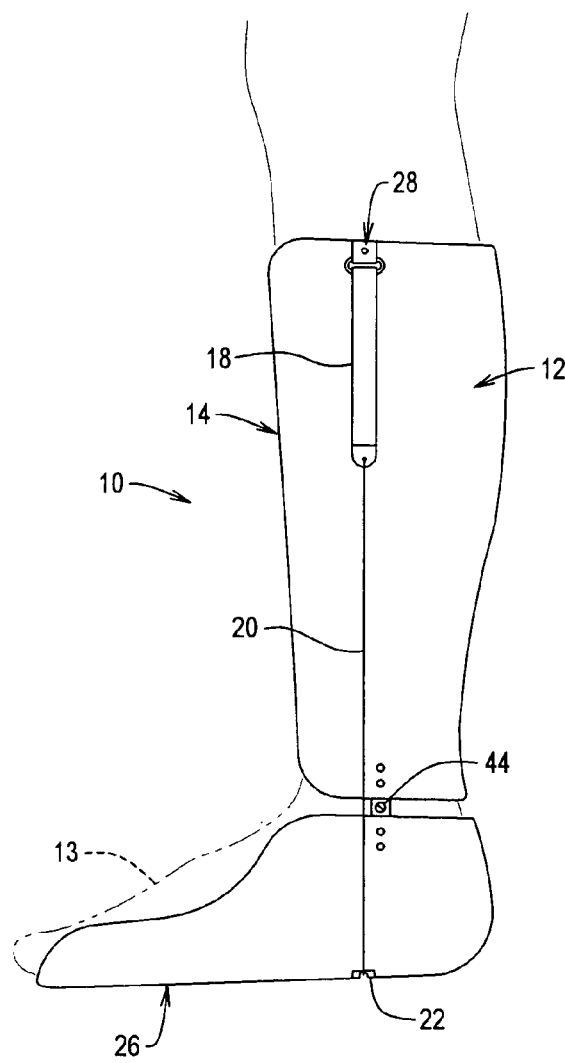
FIG. 1A is an elevational view of an ankle foot orthotic (AFO) assembly filled with a dorsiflexion assist device in accordance with the present invention, showing the cable and elastic member that generate dorsiflexion torque against the foot portion of the AFO.

The present invention provides an apparatus having, without limitation the following advantages: The ability to adapt pre-existing, conventional AFOs to have dorsiflexion assist. The ability to remove dorsiflexion assist on an AFO and thus return it to conventional operation. Providing torque that increases in force as the foot is dorsiflexed. Permitting the strength of the torque to be adjusted to meet a patient's specific needs. The ability to change the emphasis of the torque throughout the dorsiflexion of the foot.

In a preferred embodiment, the device includes the following parts, not all of which may be present in some embodiments:

(a) An elastic member mounted to the ankle section of the AFO that elongates in order to produce the tension needed to create torque.
(b) A cable that transmits the tension from the elastic member to the foot section of the AFO.
(c) An attachment that connects the cable to the foot section of the AFO at a location which is spaced anteriorly from the hinge or pivot point of the AFO.
(d) A tension adjustment device to increase or decrease tension on the elastic member.
(e) An optional cable guard, which also serves to increase cable tension.

The tension assembly is attached to the AFO above and below, and anteriorly of, the hinge point of the AFO; the anterior placement creates the dorsiflexion torque. During the range of motion, the tension exerted on the pivot arms decreases with the shortening of the elastic material, which normally tends to decrease the amount of torque; however, the present invention minimizes the effect of the decreased tension by providing a large height-to-moment arm ratio at the standing position. Consequently, as tension decreases the length of the moment arm increases, which increases the amount of force produced. The decrease in tension due to shortening is thus offset by the increase to the length of the moment arm through the range of dorsiflexion. This allows torque to be maintained or increased. depending on attachment placement.

As noted above, the device includes one or more elastic members that are attached to the foot and ankle section of the AFO. The elastic member is pre-stressed so that it will exert tension on the cable throughout the range of motion. Examples of suitable elastic materials include, but are not limited to, springs, rubber bands and tubing. The elastic material's K-value can be used to influence tension. By using low K-value material the device will undergo relatively little change in tension through the range of motion, although the material will need to be pre-stressed and lengthened to a greater extent as compared with a high K-value material, which by contrast will exhibit a more pronounced decrease of tension as its length decreases.

For the reasons explained in the preceding paragraph, it is generally desirable for this material to have a K-value that is as low as possible while avoiding elongation that would result in plasticity or deformation of the material. If plasticity occurs, the amount of tension will decrease over time and so will performance of the device. Having a low K-value will allow the material to be elongated more, and therefore the loss of length that occurs with dorsiflexion results in a lower percentage of decreased tension exerted on the cable.

The cable attaches the elastic material to the foot section of the AFO. It is desirable for the cable to be made of a durable material, for example a cable with a core of titanium, Kevlar™ or other high tension material. It is also desirable for the cable to be coated with a plastic or similar material so as to decrease friction and wear when in contact with the polyurethane or other material of the AFO. Another desirable trait for many embodiments is for the cable to have some degree of elasticity: This will allow the main elastic portion to have a larger K-value and therefore increased durability. Several cable materials conventionally used for tennis racquet cables exhibit the combination of characteristics listed above.

The cable is attached to the bottom of the arch of the foot section of the AFO, anterior to the hinge. There is a direct correlation between the location of the cable attachment and the torque that is produced throughout range of the motion of the AFO: The more inferior the attachment is in relation to the hinge, the larger the increase of torque as the AFO is dorsiflexed from the neutral position. This increase of torque results from the increase in the length of the moment arm. Increasing the anterior placement of the attachment will result in an increased resting torque. The resulting torque throughout dorsal flexion will be increased as a whole but the rate of increase in torque will be lessened; if placement is too far forward there may be a decrease in torque as dorsiflexion progresses, which is undesirable and is a weakness of previous designs.

The tension adjustment device permits the individual to increase or decrease the amount of tension that the elastic member exerts on the AFO, to increase or decrease the amount of dorsiflexion assist. This allows a patient to customize an AFO to their needs, as well as easing installation and removal of the AFO. The tensioner may be of any suitable type, with step buckles or small ratcheting strap tightening devices, similar to those found on a snowboard boot, being two examples.

As noted above, the assembly may optionally include a cable guard. The guard serves to prevent the shoe from interfering with the cable attached to the bottom of the AFO. In addition, the guard can serve as a tension amplification device and as a plantarflexion stop. With regard to this last aspect, it will be understood that, restricting plantar flexion is sometimes needed. In the prior art the conventional approach has been to install stops on the heel of the AFO typically using a compression material; this material is under significant stress and quickly wears out, and also generates noise. Moreover, it causes an abrupt stop to the motion of the foot, which can cause damage to the AFO as well as placing undue stress on to the patient's ankle and knee.

With regard to the tension amplification feature, the guard is able to catch the cable at a predetermined location, so that the upper leg of the cable is restrained against further movement in a posterior direction. This stopping of the cable increases dorsiflexion torque in two ways, i.e., by increasing the rate of elastic lengthening, resulting in more tension, and providing an additional moment arm to apply force. The result is that the bottom section of the AFO is in essence converted into a cam.

FIG. 1A illustrates an AFO 10 incorporating a dorsiflexion assist device 12 in accordance with a preferred embodiment of the present invention, with the location of the wearer's foot being indicated by dotted line image 13.

Figure 1B:
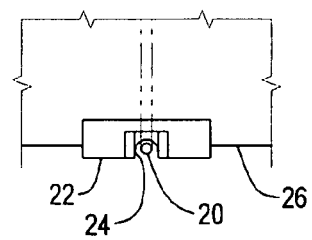
FIG. 1B is a partial, enlarged view of the bottom portion of the assembly of FIG. 1A, showing the bridge piece having a slot-like channel or groove that engages and guides the cable across the plantar surface of the foot portion of the AFO.

As can be seen, the upper end of the assist device 12 is attached to the upper part of the ankle section 14 of the AFO. The elastic member of the device is shown at 18 and the cable at 20. The bridge is at 22 and is shown in greater detail in FIG. 1B. FIG. 1B also shows the channel 24 that retains the cable and protects the cable from friction and also protects the foot section 16 of the AFO from the cable; the channel 24 also maintains the proper anterior placement of the cable so that it produces the desired torque.

Figure 2A:
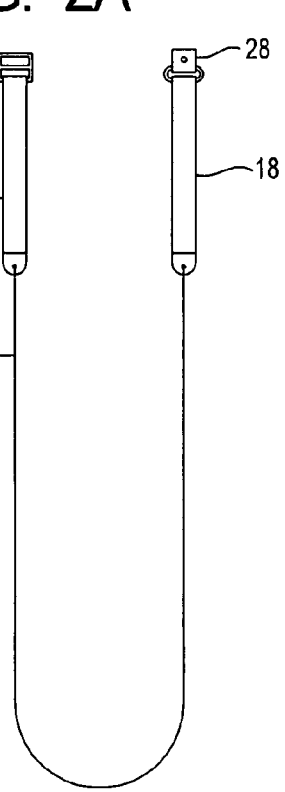
FIG. 2A is an elevational view of the cable and elastomeric strap members of the assembly of FIG. 1A.

FIG. 2A shows the dorsiflexion assist device 12 detached from the AFO. Hanger 28 is the part of the device that attaches to the ankle section of the AFO using, for example, a rivet, screw, bolt or other fastener. The elastic member 18 is responsible for creating the tension for the device. As noted above, the elastic member is suitably formed of an elastomeric band or strip, with fittings formed or mounted at its ends for attachment to the cable and to the ankle section of the AFO. Although a single, elastic member may be used, the device preferably includes first and second elastic members on opposite sides of the ankle section, as will be described below.

Cable 20 is responsible for transmitting the tension from the elastic member to the lower, foot section 26 of the AFO. There may be first and second cables that attach directly to the sides of the foot section of the AFO, or, as is shown, there may be a single cable that extends under the foot section and attaches to a second elastic member 30 on the opposite side, thus providing uniform tension on both sides of the AFO.

Figures 2B, 2C:
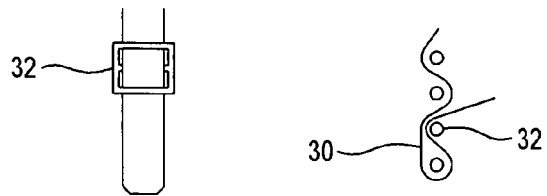
FIGS. 2B-2C are elevational and cross-sectional views of an end portion of one of the elastomeric strap members of FIG. 2A, and the buckle of the dorsiflexion assist device assembly in which the end of the elastic member is received so as to permit adjustment of the tension on the member.

Element 32 in FIG. 2B is the device for tightening the elastic member, and may be, for example, a conventional strap buckle. The strap buckle is mounted to the AFO, e.g., in the same fashion as hanger 28, and interfaces with the strap in the manner depicted in FIG. 2C. It will be understood that other tightening devices and systems may be used in place of the buckle, such as ratcheting strap devices that are commonly found on snowboard boots, for example.

Figure 3A:
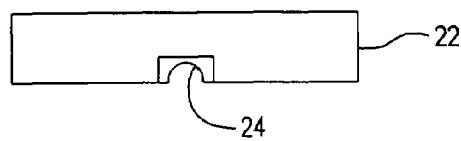
FIGS. 3A-3C are, respectively, side elevational, front elevational, and bottom plan views of the bridge piece of the assembly of FIG. 1A, showing the bridge piece and the cable slot therein in greater detail.
Figure 3B:
Figure 3C:
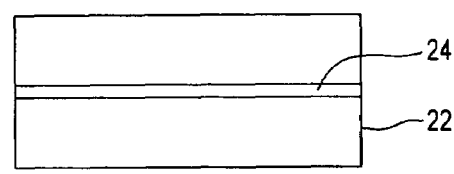
Figure 4A:
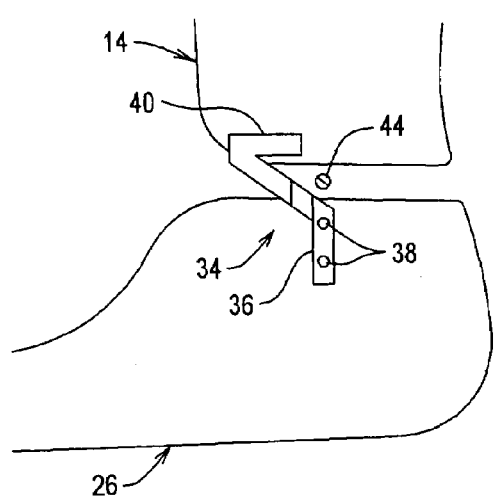
FIG. 4A is an elevational view of a cable guard that can be optionally fitted to the AFO assembly of FIG. 1A, to guide/protect the cable and also interact therewith during plantar flexion of the foot section of the assembly.
Figure 4B:
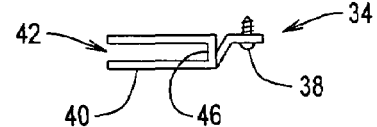
FIGS. 4B-4D are, respectively, top plan, side elevational, and front elevational views of the cable guard of FIG. 4A, showing the guide channel and mounting portions thereof in greater detail.
Figure 4C:
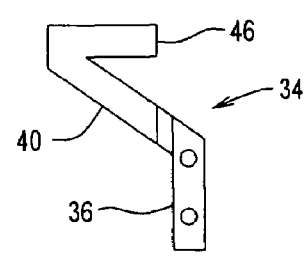
Figure 4D:
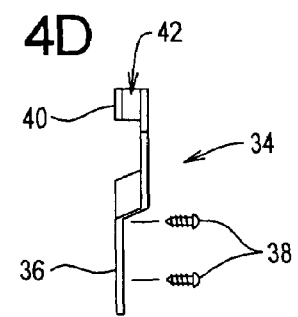

FIGS. 3A-3C show, respectively, side, front and bottom views of the bridge piece 32 that is mounted on the bottom of the foot section of the AFO, as shown in FIG. 1B. The placement of this component determines the placement of the moment arm through which the cable creates dorsiflexion torque: The further anterior the bridge is placed, the larger the neutral position torque. Further anterior placement also changes the relationship of torque throughout the motion of dorsiflexion.

FIGS. 4A-4D show the cable guard 34 in greater detail. As noted above, this component is optional and prevents interference with the cable, as well as also helping create resistance to plantar-flexion. As can be seen, the guard 34, which is suitably formed of metal or other durable, wear-resistant material, includes a base portion 36 that lies flat against the side of the foot section 26 of the AFO, and that is secured thereto by screws 38 or other suitable fasteners. A guide portion 40 of the guard extends upwardly from the base portion, generally alongside the ankle section 14 of the AFO, but is free from attachment to the latter. The guide portion of the guard includes a forwardly facing channel 42 (see FIGS. 4B and 4D), which receives the cable and extends above and forwardly of the hinge connection 44 that joins the foot and ankle portions of the AFO. As will be described below, the channel 42 of the guide portion captures and contains the cable of the assembly while allowing a degree of front-to-rear movement of the cable therein, with movement in the rearward direction being limited by the closed end wall 46 of the channel.

Figure 5A:
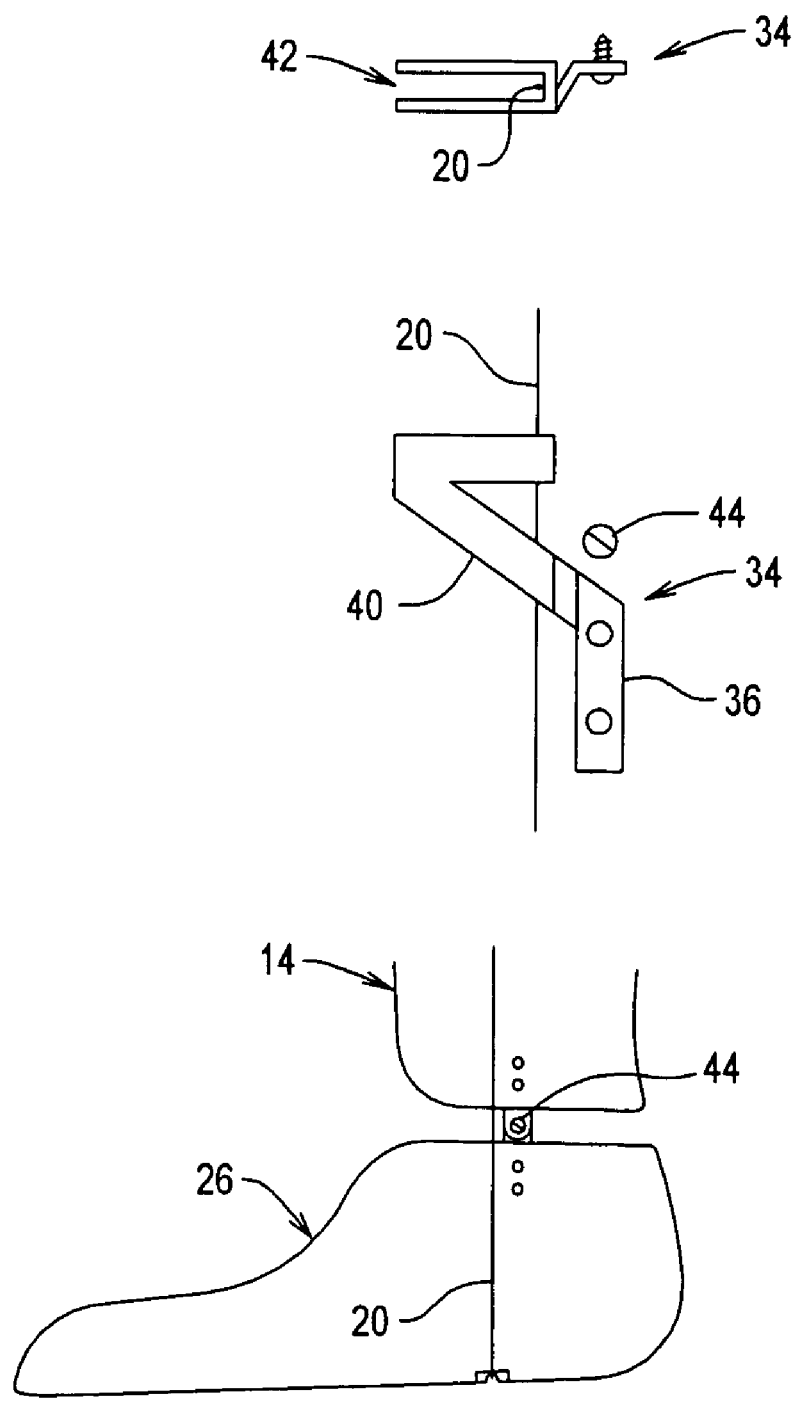
FIGS. 5A-5C are a series of plan and elevational views of a lower portion of the AFO assembly fitted with the cable guard of FIGS. 4A-4D, illustrating the interaction of the cable with the guard as the assembly moves between neutral, the dorsiflexed and plantar-flexed positions.
Figure 5B:
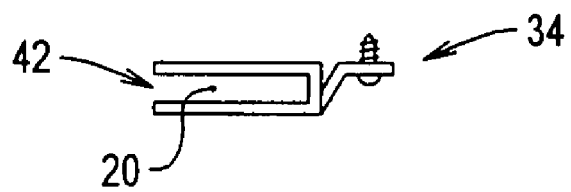
Figure 5B:
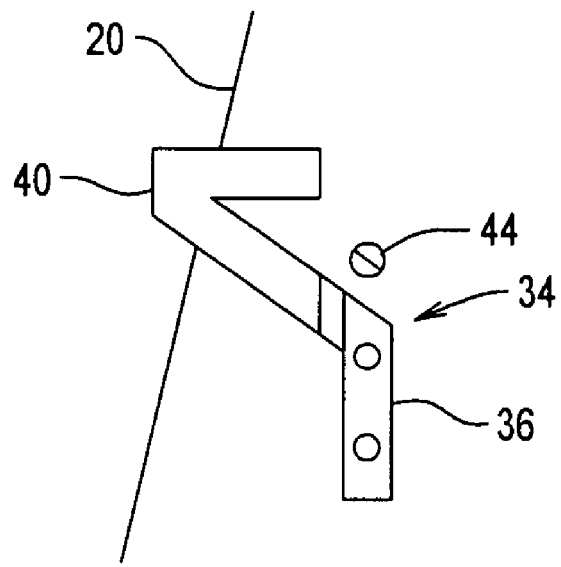
Figure 5B:
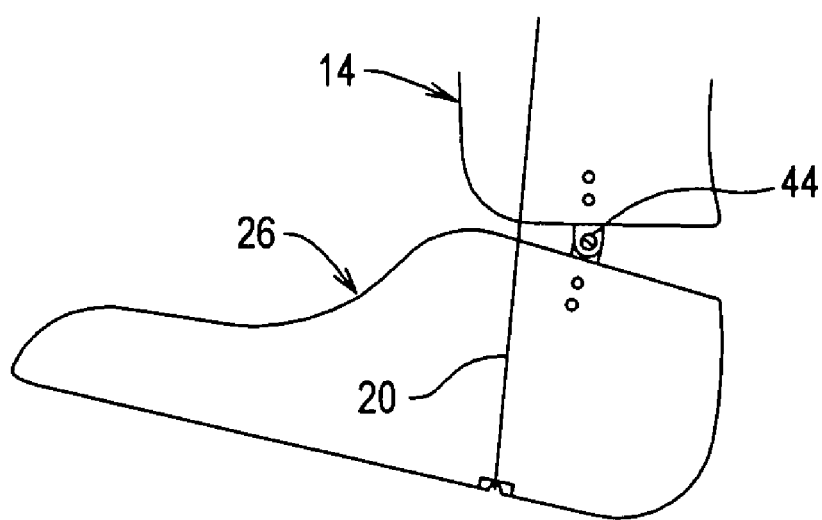
Figure 5C:
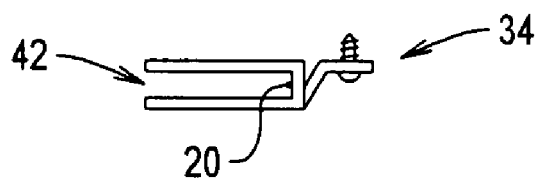
Figure 5C:
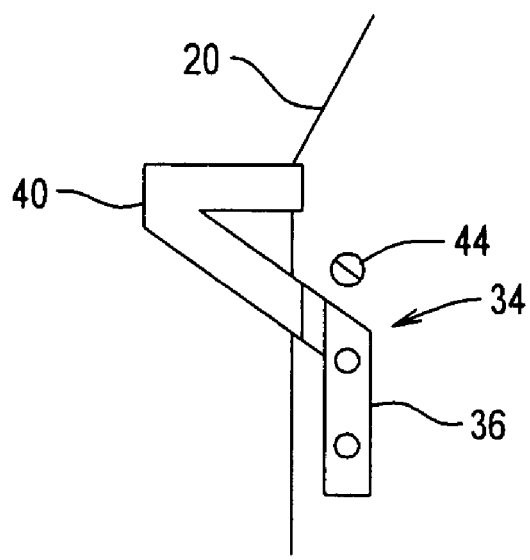
Figure 5C:
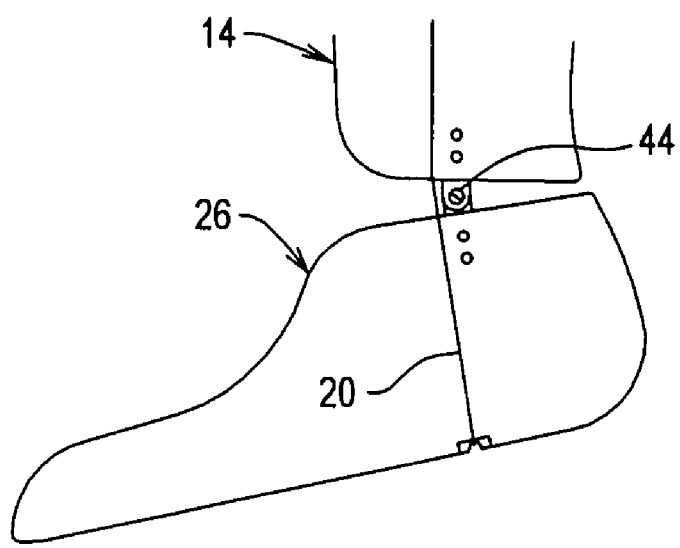

FIGS. 5A-5C illustrate operation of the guard and its interaction with the cable 20. The three positions in which the AFO are depicted are neutral position (FIG. 5A), dorsiflexion (FIG. 5B), and plantar flexion (FIG. 5C). As can be seen, when the AFO is in the neutral position, and also during dorsiflexion, the cable rides freely within the channel portion 42 and does not interface with the guard, so that the torque is not influenced by this component during these phases. However, when the AFO is plantarflexed, as is shown in FIG. 5C, the cable engages the guard, thus changing the position of the moment arm that is used to produce the torque, and causing a rapid increase in the dorsiflexion torque that is exerted on the AFO. This effect is compounded by the fact that the tension on the cable is also increasing at a greater rate than previously, due to increased elongation of the elastic member.

Figure 6A:
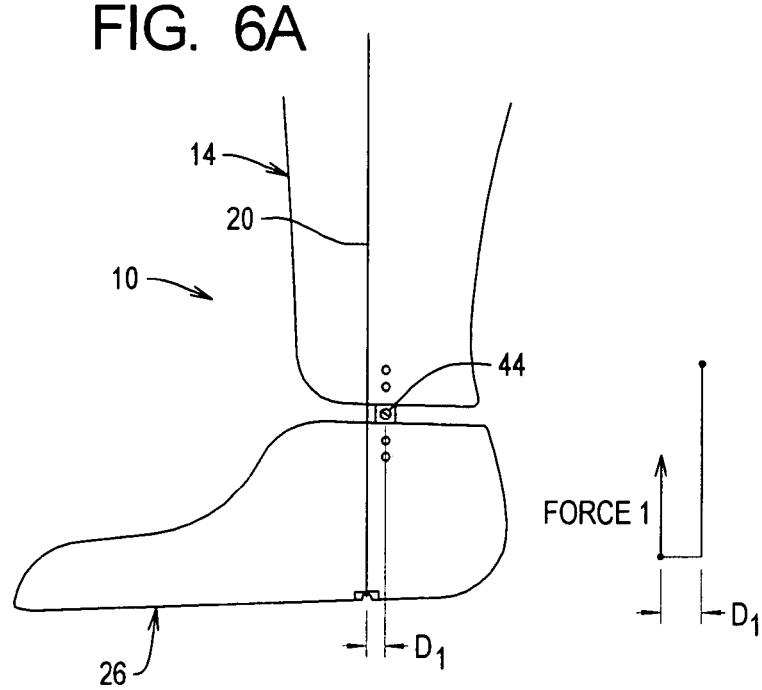
FIGS. 6A-6B are side, elevational views of the AFO assembly of FIG. 1A, with accompanying vector diagrams, illustrating the manner in which the anterior spacing between the cable attachment point and the hinge connection of the AFO affects the torque that is generated by the assembly.
Figure 6B:
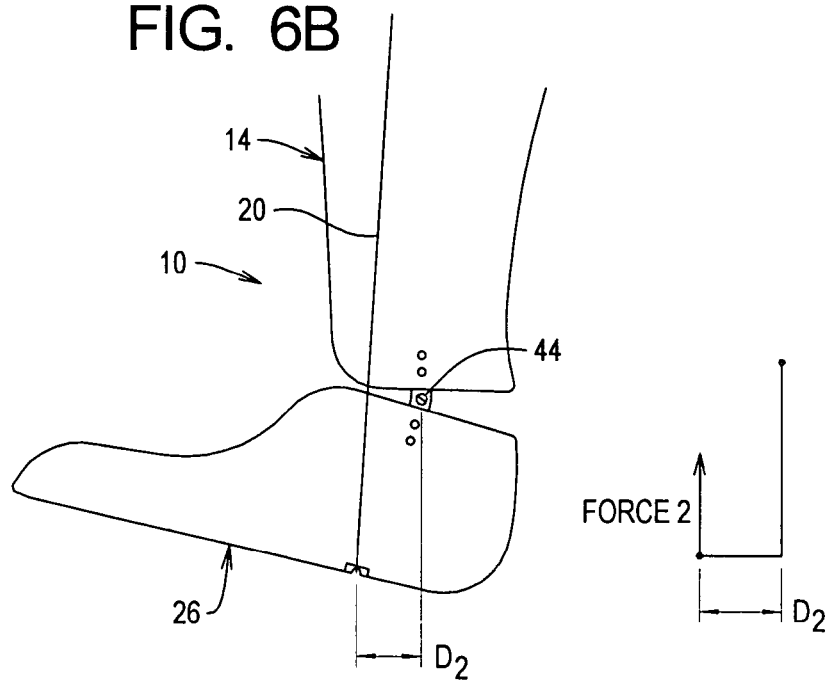

FIGS. 6A-6B illustrate the reasons for the increased torque as the ankle is dorsiflexed. In FIG. 6A the AFO is in the neutral position. At this point, the anterior-poterior distance D1 between the cable is minimal. This distance multiplied by the force exerted on the AFO by the elastic member and the cable equals the resulting torque. In 6B the distance (D2) is increased, creating a larger moment arm for the force to be exerted upon. This results in the increase of torque. As the AFO is dorsiflexed the elastic material is shortened, and as a result the force is decreased in the position shown in FIG. 6B. This force decrease is directly related to the K-value of the elastic material; if care is taken to use a lower K-value material, the force decrease due to shortening will be minimal. The equation to determine Torque is (Force*Moment arm=Torque); the force equation is (Elongation*K-value=force(tension))

Figure 7A:
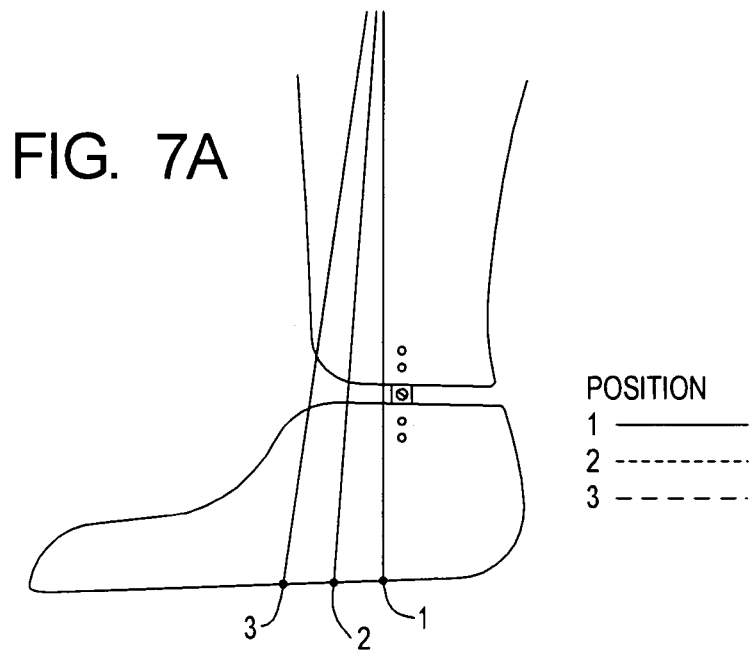
FIG. 7A is a partial, elevational view of an AFO assembly in accordance with the present invention, showing the three cable attachments at differing anterior locations.
Figure 7B:
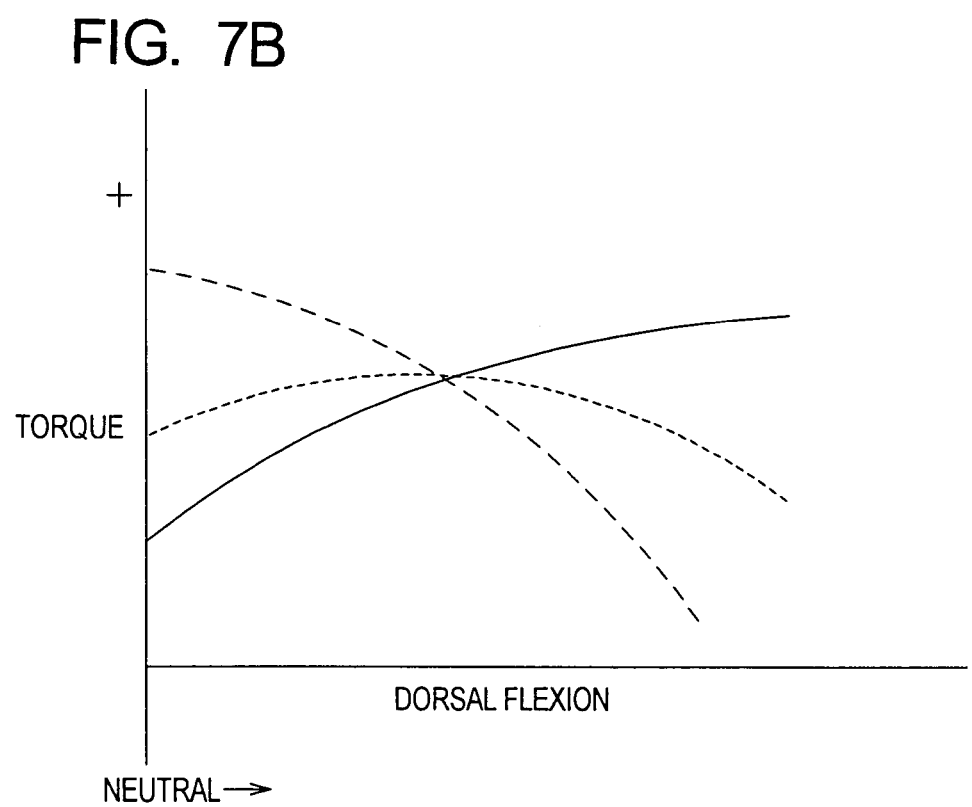
FIG. 7B is a graph of torque curves, illustrating the affect of the differing anterior locations of the cable attachment point, as shown in FIG. 7A, on torque that is generated during dorsiflexion of the AFO.

FIG. 7A shows three different placements (1, 2, 3) for the cable attachment, with 3 being the furthest anterior and 1 being the least anterior. FIG. 7B, in turn, is a graph demonstrating how these differing anterior placements affect the progression of torque throughout dorsiflexion. The torque curve yielded by position 1 would be most beneficial in most cases, but the other positions may be beneficial to meet specific, individual needs. Increasing the K-value of the elastic material has a similar effect as increasing the anterior placement of the cable.

Figure 8A:
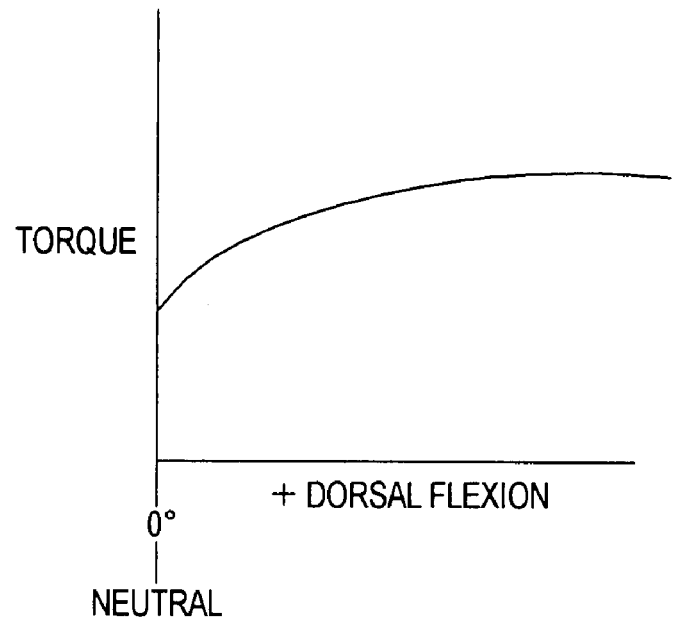
FIGS. 8A-8B are graphs comparing the torque curves produced by the AFO assembly of the present invention with that produced by a prior art dorsifexion assist device, during dorsiflexion of the two assemblies.
Figure 8B:
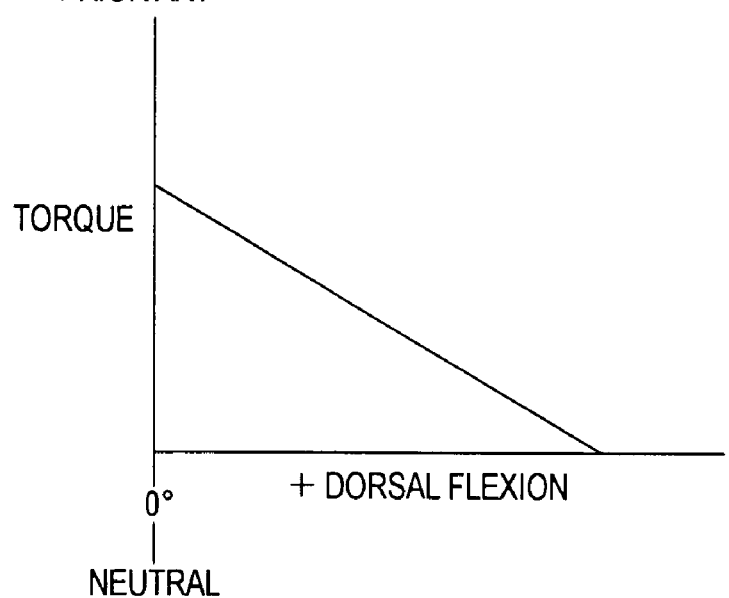

FIGS. 8A and 8B are comparative torque curve graphs demonstrating the difference in response between the apparatus of the present invention and the prior art Tamarack™ joint. As can be seen, the device of the present invention maintains and even increases the amount of torque throughout dorsiflexion, while the Tamarack™ joint does not. This increase in torque is beneficial to the patient in most cases It is to be recognized that various alterations, modifications, and/or additions may be introduced into the constructions and arrangements of parts described above without departing from the spirit or ambit of the present invention.

What is claimed is:

1. An orthotic assembly that provides dorsiflexion assistance, said orthotic assembly comprising:
    an ankle section;
    a foot section;
    a hinge connection interconnecting said ankle section and said foot section;
    at least one elastic member having a first end that is attached to said ankle section; and
    at least one cable member having a first end that is attached to a second end of said elastic member, and a second end that is attached to said foot section of said orthotic assembly at a location spaced anteriorly from said hinge connection;
    so that tension exerted on said cable member by said elastic member creates dorsiflexion torque about said hinge connection of said orthotic assembly.

2. The assembly of claim 1, further comprising:
    means for adjusting tension on said at least one elastic member.

3. The assembly of claim 2, wherein said at least one elastic member comprises:
    first and second elastic members mounted on opposite sides of said ankle section of said orthotic assembly.

4. The assembly of claim 2, wherein said means for attaching said first end of said elastic member to said ankle section of said orthotic assembly comprises:
    means for attaching said first end of said elastic member to an upper portion of said ankle section of said assembly at a location spaced anteriorly from said hinge connection.

5. The assembly of claim 2, wherein said means for attaching said cable member to said foot section of said orthotic assembly comprises:
    a bridge formed across a bottom surface of said foot section of said orthotic assembly, under which said cable member passes so that tension on said cable member is equalized on opposite sides of said orthotic assembly.

6. The assembly of claim 5, wherein said bridge comprises:
    a transversely extending channel that receives said cable member therein.

7. The assembly of claim 2, further comprising:
    a cable guard that is mounted to said foot section of said orthotic assembly so as to prevent interference with said cable member.

8. The assembly of claim 7, wherein said guard member comprises:
    a generally vertically extending channel portion that captures said cable member so as to arrest rearward movement of said cable member at a predetermined location, so as to create a moment arm that compensates for reduced tension resulting from shortening of said elastic member during dorsiflexion of said foot section of said assembly.

9. A method for providing dorsiflexion assistance in an orthotic device having an ankle section and a foot section interconnected by a hinge connection, said method comprising the steps of:
provoding a dorsiflexion assistance apparatus comprising:
an elastic member having a first end and a second end; and
a cable member having first and second ends, said first end of said cable member being attached to said second end of said elastic member;
attaching said first end of said elastic member to said ankle section of said orthotic device; and
attaching said second end of said cable member to said foot section of said orthotic device at a position spaced anteriorly from said hinge connection;
so that tension created on said cable member by said elastic member creates dorsiflexion torque about said hinge connection of said orthotic device.

* * * * *